us006165782A

United States Patent [19]
Naldini et al.

[11] Patent Number: 6,165,782
[45] Date of Patent: *Dec. 26, 2000

[54] METHOD AND MEANS FOR PRODUCING HIGH TITER, SAFE, RECOMBINANT LENTIVIRUS VECTORS

[75] Inventors: Luigi Naldini, San Carlos; Thomas Dull, San Francisco; Deborah A. Farson, Oakland; Rochelle Witt, San Francisco, all of Calif.

[73] Assignee: Cell Genesys, Inc., Foster City, Calif.

[ * ] Notice: This patent is subject to a terminal disclaimer.

[21] Appl. No.: 09/271,365

[22] Filed: Mar. 18, 1999

Related U.S. Application Data

[62] Division of application No. 08/989,394, Dec. 12, 1997, Pat. No. 5,994,136.

[51] Int. Cl.⁷ .................................................... C12N 15/867
[52] U.S. Cl. ........................ 435/320.1; 435/455; 435/456
[58] Field of Search ................................. 435/320.1, 69.1, 435/325, 455, 456, 462, 463, 366, 369

[56] References Cited

PUBLICATIONS

Elder et al., Adv. Virus Res., vol. 45, pp. 225–247, 1995.

*Primary Examiner*—David Guzo
*Attorney, Agent, or Firm*—Roylance, Abrams, Berdo & Goodman, L.L.P.

[57] ABSTRACT

Lentiviral vectors modified at the 5' LTR or both the 5' and 3' LTR's are useful in the production of recombinant lentivirus vectors. Such vectors can be produced in the absence of a functional tat gene. Multiple transformation of the host cell with the vector carrying the transgene enhances virus production.

9 Claims, 3 Drawing Sheets

METHOD AND MEANS FOR PRODUCING HIGH TITER, SAFE, RECOMBINANT LENTIVIRUS VECTORS

This is a divisional of application Ser. No. 08,989,394 filed Dec. 12, 1997, now U.S. Pat. No. 5,994,136, the disclosure of which is incorporated herein by reference.

FIELD OF THE INVENTION

The invention relates to novel lentiviral packaging vectors, transfer vectors carrying a foreign gene of interest, stable packaging cell lines, stable producer cell lines and the use thereof for producing recombinant lentivirus in mammalian cells.

BACKGROUND OF THE INVENTION

Retrovirus vectors are a common tool for gene delivery (Miller, Nature (1992) 357:455–460). The ability of retrovirus vectors to deliver an unrearranged, single copy gene into a broad range of rodent, primate and human somatic cells makes retroviral vectors well suited for transferring genes to a cell.

A useful adjunct for producing recombinant retroviral vectors are packaging cell lines which supply in trans the proteins necessary for producing infectious virions, but those cells are incapable of packaging endogenous viral genomic nucleic acids (Watanabe & Temin, Molec. Cell. Biol. (1983) 3(12):2241–2249; Mann et al., Cell (1983) 33:153–159; Embretson & Temin, J. Virol. (1987) 61(9):2675–2683). A consideration in the construction of retroviral packaging cell lines is the production of high titer vector supernatants free of recombinant replication competent retrovirus (RCR), which have been shown to produce T cell lymphomas in rodents (Cloyd et al., J. Exp. Med. (1980) 151:542–552) and in primates (Donahue et al., J. Exp. Med. (1992) 176:1125–1135).

One approach to minimize the likelihood of generating RCR in packaging cells is to divide the packaging functions into two genomes, for example, one which expresses the gag and pol gene products and the other which expresses the env gene product (Bosselman et al., Molec. Cell. Biol. (1987) 7(5):1797–1806; Markowitz et al., J. Virol. (1988) 62(4):1120–1124; Danos & Mulligan, Proc. Natl. Acad. Sci. (1988) 85:6460–6464). That approach minimizes the ability for co-packaging and subsequent transfer of the two-genomes, as well as significantly decreasing the frequency of recombination due to the presence of three retroviral genomes in the packaging cell to produce RCR.

In the event recombinants arise, mutations (Danos & Mulligan, supra) or deletions (Boselman et al., supra; Markowitz et al., supra) can be configured within the undesired gene products to render any possible recombinants non-functional. In addition, deletion of the 3' LTR on both packaging constructs further reduces the ability to form functional recombinants.

Lentiviruses are complex retroviruses which, in addition to the common retroviral genes gag, pol and env, contain other genes with regulatory or structural function. The higher complexity enables the lentivirus to modulate the life cycle thereof, as in the course of latent infection.

A typical lentivirus is the human immunodeficiency virus (HIV), the etiologic agent of AIDS. In vivo, HIV can infect terminally differentiated cells that rarely divide, such as lymphocytes and macrophages. In vitro, HIV can infect primary cultures of monocyte-derived macrophages (MDM) as well as HeLa-Cd4 or T lymphoid cells arrested in the cell cycle by treatment with aphidicolin or γ irradiation.

Infection of cells is dependent on the active nuclear import of HIV preintegration complexes through the nuclear pores of the target cells. That occurs by the interaction of multiple, partly redundant, molecular determinants in the complex with the nuclear import machinery of the target cell. Identified determinants include a functional nuclear localization signal (NLS) in the gag matrix (MA) protein, the karyophilic virion-associated protein, vpr, and a C-terminal phosphotyrosine residue in the gag MA protein.

SUMMARY OF THE INVENTION

Accordingly, the instant invention relates to novel disarmed lentiviral vectors that direct the synthesis of both lentiviral vector transcripts which can be packaged and lentiviral proteins for rapid production of high titer recombinant lentivirus in mammalian cells. The results are infectious particles for delivering a foreign gene of interest to a target cell. The invention also provides cell lines for virus production.

DETAILED DESCRIPTION OF THE INVENTION

Figure 1:
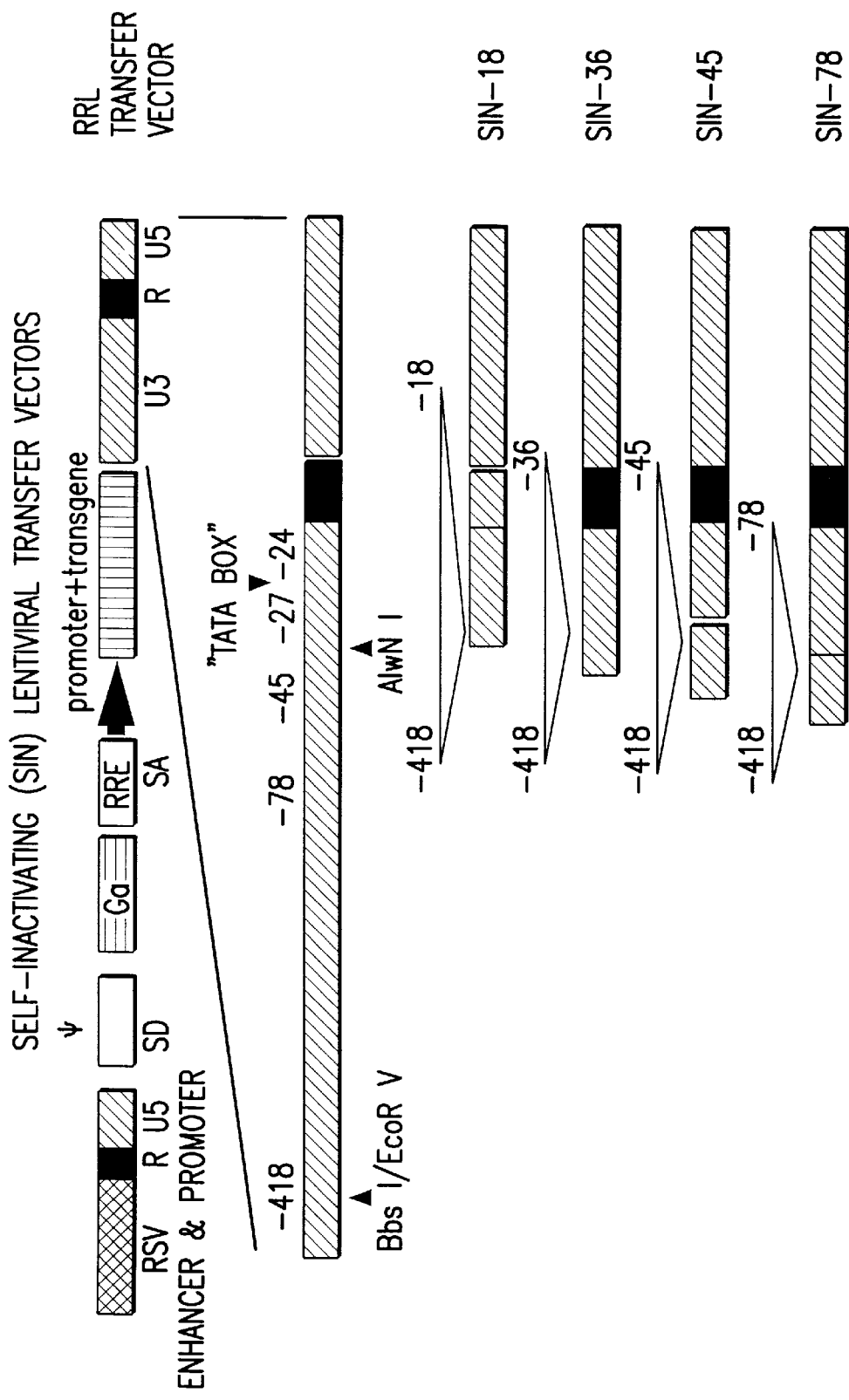
FIG. 1 depicts various lentivirus vectors. RSV is the Rous sarcoma virus enhancer/promoter; R is the R region of the LTR; U5 is the U5 region of the LTR; SD is a slice donor site, such as the HIV 5' major splice donor site; ψ is the Psi encapsidation signal sequence; Ga is a part of the gag gene; RRE is the rev responsive element; SA is a splice acceptor sequence; and U3 is the U3 region of the LTR.

The instant invention provides a recombinant lentivirus capable of infecting non-dividing cells as well as methods and means for making same. The virus is useful for the in vivo and ex vivo transfer and expression of nucleic acid sequences.

The lentiviral genome and the proviral DNA have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins.

The invention provides a method of producing a recombinant lentivirus capable of infecting a non-dividing cell comprising transfecting a suitable host cell with two or more vectors carrying the packaging functions, namely gag, pol and env, as well as rev and tat. As will be disclosed hereinbelow, vectors lacking a functional tat gene are desirable for certain applications. Thus, for example, a first vector can provide a nucleic acid encoding a viral gag and a viral pol and another vector can provide a nucleic acid encoding a viral env to produce a packaging cell. Introducing a vector providing a heterologous gene, herein identified as a transfer vector, into that packaging cell yields a producer cell which releases infectious viral particles carrying the foreign gene of interest.

The vectors per se, outside of the newly constructed vectors disclosed herein, are known in the art, see Naldini et al., Sci. (1996) 272:263–267; and Zufferey et al., Nat. Biotech. (1997) 15:871–875. Generally the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest.

According to the above-indicated configuration of vectors and foreign genes, the second vector can provide a nucleic acid encoding a viral envelope (env) gene. The env gene can be derived from any virus, including retroviruses. The env preferably is an amphotropic envelope protein which allows transduction of cells of human and other species.

It may be desirable to target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific. Retroviral vectors can be made target-specific by inserting, for example, a glycolipid or a protein. Targeting often is accomplished by using an antigen-binding portion of an antibody or a recombinant antibody-type molecule, such as a single chain antibody, to target the retroviral vector. Those of skill in the art will know of, or can readily ascertain without undue experimentation, specific methods to achieve delivery of a retroviral vector to a specific target.

Examples of retroviral-derived env genes include, but are not limited to: Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). Other env genes such as Vesicular stomatitis virus (VSV) protein G (VSV G), that of hepatitis viruses and of influenza also can be used.

The vector providing the viral env nucleic acid sequence is associated operably with regulatory sequences, e.g., a promoter or enhancer. The regulatory sequence can be any eukaryotic promoter or enhancer, including for example, the Moloney murine leukemia virus promoter-enhancer element, the human cytomegalovirus enhancer or the vaccinia P7.5 promoter. In some cases, such as the Moloney murine leukemia virus promoter-enhancer element, the promoter-enhancer elements are located within or adjacent to the LTR sequences.

Preferably, the regulatory sequence is one which is not endogenous to the lentivirus from which the vector is being constructed. Thus, if the vector is being made from SIV, the SIV regulatory sequence found in the SIV LTR would be replaced by a regulatory element which does not originate from SIV.

While VSV G protein is a desirable env gene because VSV G confers broad host range on the recombinant virus, VSV G can be deleterious to the host cell. Thus, when a gene such as that for VSV G is used, it is preferred to employ an inducible promoter system so that VSV G expression can be regulated to minimize host toxicity when VSV G is expression is not required.

For example, the tetracycline-regulatable gene expression system of Gossen & Bujard (Proc. Natl. Acad. Sci. (1992) 89:5547–5551) can be employed to provide for inducible expression of VSV G when tetracycline is withdrawn from the transferred cell. Thus, the tet/VP16 transactivator is present on a first vector and the VSV G coding sequence is cloned downstream from a promoter controlled by tet operator sequences on another vector.

The heterologous or foreign nucleic acid sequence, the transgene, is linked operably to a regulatory nucleic acid sequence. As used herein, the term "heterologous" nucleic acid sequence refers to a sequence that originates from a foreign species, or, if from the same species, it may be substantially modified from the original form. Alternatively, an unchanged nucleic acid sequence that is not expressed normally in a cell is a heterologous nucleic acid sequence.

The term "operably linked" refers to functional linkage between a regulatory sequence and a heterologous nucleic acid sequence resulting in expression of the latter. Preferably, the heterologous sequence is linked to a promoter, resulting in a chimeric gene. The heterologous nucleic acid sequence is preferably under control of either the viral LTR promoter-enhancer signals or of an internal promoter, and retained signals within the retroviral LTR can still bring about efficient expression of the transgene.

The foreign gene can be any nucleic acid of interest which can be transcribed. Generally the foreign gene encodes a polypeptide. Preferably the polypeptide has some therapeutic benefit. The polypeptide may supplement deficient or nonexistent expression of an endogenous protein in a host cell. The polypeptide can confer new properties on the host cell, such as a chimeric signalling receptor, see U.S. Pat. No. 5,359,046. The artisan can determine the appropriateness of a foreign gene practicing techniques taught herein and known in the art. For example, the artisan would know whether a foreign gene is of a suitable size for encapsidation and whether the foreign gene product is expressed properly.

It may be desirable to modulate the expression of a gene regulating molecule in a cell by the introduction of a molecule by the method of the invention. The term "modulate" envisions the suppression of expression of a gene when it is over-expressed or augmentation of expression when it is under-expressed. Where a cell proliferative disorder is associated with the expression of a gene, nucleic acid sequences that interfere with the expression of a gene at the translational level can be used. The approach can utilize, for example, antisense nucleic acid, ribozymes or triplex agents to block transcription or translation of a specific mRNA, either by masking that mRNA with an antisense nucleic acid or triplex agent, or by cleaving same with a ribozyme.

Antisense nucleic acids are DNA or RNA molecules which are complementary to at least a portion of a specific mRNA molecule (Weintraub, Sci. Am. (1990) 262:40). In the cell, the antisense nucleic acids hybridize to the corresponding mRNA forming a double-stranded molecule. The antisense nucleic acids interfere with the translation of the mRNA since the cell will not translate a mRNA that is double-stranded. Antisense oligomers of about 15 nucleotides or more are preferred since such are synthesized easily and are less likely to cause problems than larger molecules when introduced into the target cell. The use of antisense methods to inhibit the in vitro translation of genes is well known in the art (Marcus-Sakura, Anal. Biochem. (1988) 172:289).

The antisense nucleic acid can be used to block expression of a mutant protein or a dominantly active gene product, such as amyloid precursor protein that accumulates in Alzheimer's disease. Such methods are also useful for the treatment of Huntington's disease, hereditary Parkinsonism and other diseases. Antisense nucleic acids are also useful for the inhibition of expression of proteins associated with toxicity.

Use of an oligonucleotide to stall transcription can be by the mechanism known as the triplex strategy since the oligomer winds around double-helical DNA, forming a three-strand helix. Therefore, the triplex compounds can be designed to recognize a unique site on a chosen gene (Maher et al., Antisense Res and Dev. (1991) 1(3):227; Helene, Anticancer Drug Dis. (1991) 6(6):569).

Ribozymes are RNA molecules possessing the ability to specifically cleave other single-stranded RNA in a manner analogous to DNA restriction endonucleases. Through the modification of nucleotide sequences which encode those RNA's, it is possible to engineer molecules that recognize and cleave specific nucleotide sequences in an RNA molecule (Cech, J. Amer. Med Assn. (1988) 260:3030). A major advantage of that approach is only mRNA's with particular sequences are inactivated.

It may be desirable to transfer a nucleic acid encoding a biological response modifier. Included in that category are immunopotentiating agents including nucleic acids encoding a number of the cytokines classified as "interleukins", for example, interleukins 1 through 12. Also included in that category, although not necessarily working according to the same mechanism, are interferons, and in particular gamma interferon (γ-IFN), tumor necrosis factor (TNF) and granulocyte-macrophage colony stimulating factor (GM-CSF). It may be desirable to deliver such nucleic acids to bone marrow cells or macrophages to treat inborn enzymatic deficiencies or immune defects. Nucleic acids encoding growth factors, toxic peptides, ligands, receptors or other physiologically important proteins also can be introduced into specific non-dividing cells.

Thus, the recombinant lentivirus of the invention can be used to treat an HIV-infected cell (e.g., T-cell or macrophage) with an anti-HIV molecule. In addition, respiratory epithelium, for example, can be infected with a recombinant lentivirus of the invention having a gene for cystic fibrosis transmembrane conductance regulator (CFTR) for treatment of cystic fibrosis.

The method of the invention may also be useful for neuronal, glial, fibroblast or mesenchymal cell transplantation, or "grafting", which involves transplantation of cells infected with the recombinant lentivirus of the invention ex vivo, or infection in vivo into the central nervous system or into the ventricular cavities or subdurally onto the surface of a host brain. Such methods for grafting will be known to those skilled in the art and are described in Neural Grafting in the Mammalian CNS, Bjorklund & Stenevi, eds. (1985).

For diseases due to deficiency of a protein product, gene transfer could introduce a normal gene into the affected tissues for replacement therapy, as well as to create animal models for the disease using antisense mutations. For example, it may be desirable to insert a Factor VIII or IX encoding nucleic acid into a lentivirus for infection of a muscle, spleen or liver cell.

The promoter sequence may be homologous or heterologous to the desired gene sequence. A wide range of promoters may be utilized, including a viral or a mammalian promoter. Cell or tissue specific promoters can be utilized to target expression of gene sequences in specific cell populations. Suitable mammalian and viral promoters for the instant invention are available in the art.

Optionally during the cloning stage, the nucleic acid construct referred to as the transfer vector, having the packaging signal and the heterologous cloning site, also contains a selectable marker gene. Marker genes are utilized to assay for the presence of the vector, and thus, to confirm infection and integration. The presence of a marker gene ensures the selection and growth of only those host cells which express the inserts. Typical selection genes encode proteins that confer resistance to antibiotics and other toxic substances, e.g., histidinol, puromycin, hygromycin, neomycin, methotrexate etc. and cell surface markers.

The recombinant virus of the invention is capable of transferring a nucleic acid sequence into a mammalian cell. The term, "nucleic acid sequence", refers to any nucleic acid molecule, preferably DNA, as discussed in detail herein. The nucleic acid molecule may be derived from a variety of sources, including DNA, cDNA, synthetic DNA, RNA or combinations thereof. Such nucleic acid sequences may comprise genomic DNA which may or may not include naturally occurring introns. Moreover, such genomic DNA may be obtained in association with promoter regions, poly A sequences or other associated sequences. Genomic DNA may be extracted and purified from suitable cells by means well known in the art. Alternatively, messenger RNA (mRNA) can be isolated from cells and used to produce CDNA by reverse transcription or other means.

Preferably, the recombinant lentivirus produced by the method of the invention is a derivative of human immunodeficiency virus (HIV). The env will be derived from a virus other than HIV.

The method of the invention provides, in some embodiments, three vectors which provide all of the functions required for packaging of recombinant virions, such as, gag, pol, env, tat and rev, as discussed above. As noted herein, tat may be deleted functionally for unexpected benefits. There is no limitation on the number of vectors which are utilized so long as the vectors are used to transform and to produce the packaging cell line to yield recombinant lentivirus.

The vectors are introduced via transfection or infection into the packaging cell line. The packaging cell line produces viral particles that contain the vector genome. Methods for transfection or infection are well known by those of skill in the art. After cotransfection of the packaging vectors and the transfer vector to the packaging cell line, the recombinant virus is recovered from the culture media and titered by standard methods used by those of skill in the art.

Thus, the packaging constructs can be introduced into human cell lines by calcium phosphate transfection, lipofection or electroporation, generally together with a dominant selectable marker, such as neo, DHFR, Gln synthetase or ADA, followed by selection in the presence of the appropriate drug and isolation of clones. The selectable marker gene can be linked physically to the packaging genes in the construct.

Stable cell lines wherein the packaging functions are configured to be expressed by a suitable packaging cell are known. For example, see U.S. Pat. No. 5,686,279; and Ory et al., Proc. Natl. Acad. Sci. (1996) 93:11400–11406, which describe packaging cells.

Zufferey et al., supra, teach a lentiviral packaging plasmid wherein sequences 3' of pol including the HIV-1 env gene are deleted. The construct contains tat and rev sequences and the 3' LTR is replaced with poly A sequences. The 5' LTR and psi sequences are replaced by another promoter, such as one which is inducible. For example, a CMV promoter or derivative thereof can be used.

The packaging vectors of interest contain additional changes to the packaging functions to enhance lentiviral protein expression and to enhance safety. For example, all of the HIV sequences upstream of gag can be removed. Also, sequences downstream of env can be removed. Moreover, steps can be taken to modify the vector to enhance the splicing and translation of the RNA.

To provide a vector with an even more remote possibility of generating replication competent lentivirus, the instant invention provides for lentivirus packaging plasmids wherein tat sequences, a regulating protein which promotes viral expression through a transcriptional mechanism, are deleted functionally. Thus, the tat gene can be deleted, in part or in whole, or various point mutations or other mutations can be made to the tat sequence to render the gene non-functional. An artisan can practice known techniques to render the tat gene non-functional.

The techniques used to construct vectors, and to transfect and to infect cells, are practiced widely in the art. Practitioners are familiar with the standard resource materials which describe specific conditions and procedures. However, for convenience, the following paragraphs may serve as a guideline.

Construction of the vectors of the invention employs standard ligation and restriction techniques which are well understood in the art (see Maniatis et al., in Molecular Cloning: A Laboratory Manual, Cold Spring Harbor Laboratory, N.Y., 1982). Isolated plasmids, DNA sequences or synthesized oligonucleotides are cleaved, tailored and religated in the form desired.

Site-specific DNA cleavage is performed by treating with the suitable restriction enzyme (or enzymes) under conditions which are understood in the art, and the particulars of which are specified by the manufacturer of the commercially available restriction enzymes, see, e.g. New England Biolabs, Product Catalog. In general, about 1 $\mu$g of plasmid or DNA sequences is cleaved by one unit of enzyme in about 20 $\mu$l of buffer solution. Typically, an excess of restriction enzyme is used to ensure complete digestion of the DNA substrate. Incubation times of about one hour to two hours at about 37° C. are workable, although variations can be tolerated. After each incubation, protein is removed by extraction with phenol/chloroform, which may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in Methods of Enzymology 65:499–560. (1980).

Restriction cleaved fragments may be blunt ended by treating with the large fragment of E. coli DNA polymerase I (Klenow) in the presence of the four deoxynucleotide triphosphates (dNTP's) using incubation times of about 15 to 25 minutes at 20° C. in 50 mM Tris (pH 7.6) 50 mM NaCl, 6 mM $MgCl_2$, 6 mM DTT and 5–10 $\mu$M dNTP's. The Klenow fragment fills in at 5' sticky ends but chews back protruding 3' single strands, even though the four dNTP's are present. If desired, selective repair can be performed by supplying only one of the dNTP's, or with selected dNTP's, within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Ligations can be performed in 15–50 $\mu$l volumes under the following standard conditions and temperatures: 20 mM Tris-Cl pH 7.5, 10 mM $MgCl_2$, 10 mM DTT, 33 mg/ml BSA, 10 mM-50 mM NaCl and either 40 $\mu$M ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 $\mu$g/ml total DNA concentrations (5–100 mM total end concentration). Intermolecular blunt end ligations (usually employing a 10–30 fold molar excess of linkers) are performed at 1 $\mu$M total ends concentration.

Thus, according to the instant invention, a lentiviral packaging vector is made to contain a promoter and other optional or requisite regulatory sequences as determined by the artisan, gag, pol, rev, env or a combination thereof, and with specific functional or actual excision of tat, and optionally other lentiviral accessory genes.

Lentiviral transfer vectors (Naldini et al., supra; Proc. Natl. Acad. Sci. (1996) 93:11382–11388) have been used to infect human cells growth-arrested in vitro and to transduce neurons after direct injection into the brain of adult rats. The vector was efficient at transferring marker genes in vivo into the neurons and long term expression in the absence of detectable pathology was achieved. Animals analyzed ten months after a single injection of the vector, the longest time tested so far, showed no decrease in the average level of transgene expression and no sign of tissue pathology or immune reaction. (Blomer et al., J. Virol. (1997) 71:6641–6649). An improved version of the lentiviral vector in which the HIV virulence genes env, vif, vpr, vpu and nef were deleted without compromising the ability of the vector to transduce non-dividing cells have been developed. The multiply attenuated version represents a substantial improvement in the biosafety of the vector (Zufferey et al., supra).

In transduced cells, the integrated lentiviral vector generally has an LTR at each termini. The 5' LTR may cause accumulation of "viral" transcripts that may be the substrate of recombination, in particular in HIV-infected cells. The 3' LTR may promote downstream transcription with the consequent risk of activating a cellular protooncogene.

The U3 sequences comprise the majority of the HIV LTR. The U3 region contains the enhancer and promoter elements that modulate basal and induced expression of the HIV genome in infected cells and in response to cell activation. Several of the promoter elements are essential for viral replication. Some of the enhancer elements are highly conserved among viral isolates and have been implicated as critical virulence factors in viral pathogenesis. The enhancer elements may act to influence replication rates in the different cellular target of the virus (Marthas et al. J. Virol. (1993) 67:6047–6055).

As viral transcription starts at the 3' end of the U3 region of the 5' LTR, those sequences are not part of the viral mRNA and a copy thereof from the 3' LTR acts as template for the generation of both LTR's in the integrated provirus. If the 3' copy of the U3 region is altered in a retroviral vector construct, the vector RNA still is produced from the intact 5' LTR in producer cells, but cannot be regenerated in target cells. Transduction of such a vector results in the inactivation of both LTR's in the progeny virus. Thus, the retrovirus is self-inactivating (SIN) and those vectors are known as Sin transfer vectors.

There are, however, limits to the extent of the deletion at the 3' LTR. First, the 5' end of the U3 region serves another essential function in vector transfer, being required for integration (terminal dinucleotide+att sequence). Thus, the terminal dinucleotide and the att sequence may represent the 5' boundary of the U3 sequences which can be deleted. In addition, some loosely defined regions may influence the activity of the downstream polyadenylation site in the R region. Excessive deletion of U3 sequence from the 3' LTR may decrease polyadenylation of vector transcripts with adverse consequences both on the titer of the vector in producer cells and the transgene expression in target cells. On the other hand, limited deletions may not abrogate the transcriptional activity of the LTR in transduced cells.

New versions of a lentivirus transfer vector described herein carry increasing deletions of the U3 region of the 3' LTR (FIG. 1: the U3 deletions span from nucleotide –418 of the U3 LTR to the indicated position: SIN-78, SIN-45, SIN-36 and SIN-18). Lentiviral vectors with almost complete deletion of the U3 sequences from the 3' LTR were developed without compromising either the titer of vector in producer cells or transgene expression in target cells. The most extensive deletion (–418 to –18) extends as far as to the TATA box, therefore abrogating any transcriptional activity of the LTR in transduced cells. Thus, the lower limit of the 3' deletion may extend as far as including the TATA box. The deletion may be of the remainder of the U3 region up to the R region. That represents a dramatic gain in vector safety. The various deletions were produced practicing methods known in the art.

Surprisingly, the average expression level of the transgene was even higher in cells transduced by the SIN vectors as compared to more intact vectors. That was probably due to the removal of transcriptional interference from the upstream HIV LTR on the internal promoter. SIN-type vectors with such extensive deletions of the U3 region could not be generated for murine leukemia virus (MLV) based retroviral vectors without compromising efficiency of transduction.

The 5' LTR of transfer vector construct was modified by substituting part or all of the transcriptional regulatory elements of the U3 region with heterologous enhancer/promoters. The changes were made to enhance the expression of transfer vector RNA in producer cells; to allow vector production in the absence of the HIV tat gene; and to remove the upstream wild-type copy of the HIV LTR that can recombine with the 3' deleted version to "rescue" the above described SIN vectors.

Thus, vectors containing the above-described alterations at the 5' LTR, 5' vectors, can find use as transfer vectors because of the sequences to enhance expression and in combination with packaging cells that do not express tat.

Such 5' vectors can also carry modifications at the 3' LTR as discussed hereinabove to yield improved transfer vectors which have not only enhanced expression and can be used in packaging cells that do not express tat but can be self-inactivating as well.

The transcription from the HIV LTR is highly dependent on the transactivator function of the tat protein. In the presence of tat, often expressed by the core packaging construct existing in producer cells, vector transcription from the HIV LTR is stimulated strongly. As that full-length "viral" RNA has a full complement of packaging signals, the RNA is encapsidated efficiently into vector particles and transferred to target cells. The amount of vector RNA available for packaging in producer cells is a rate-limiting step in the production of infectious vector.

Figure 2:
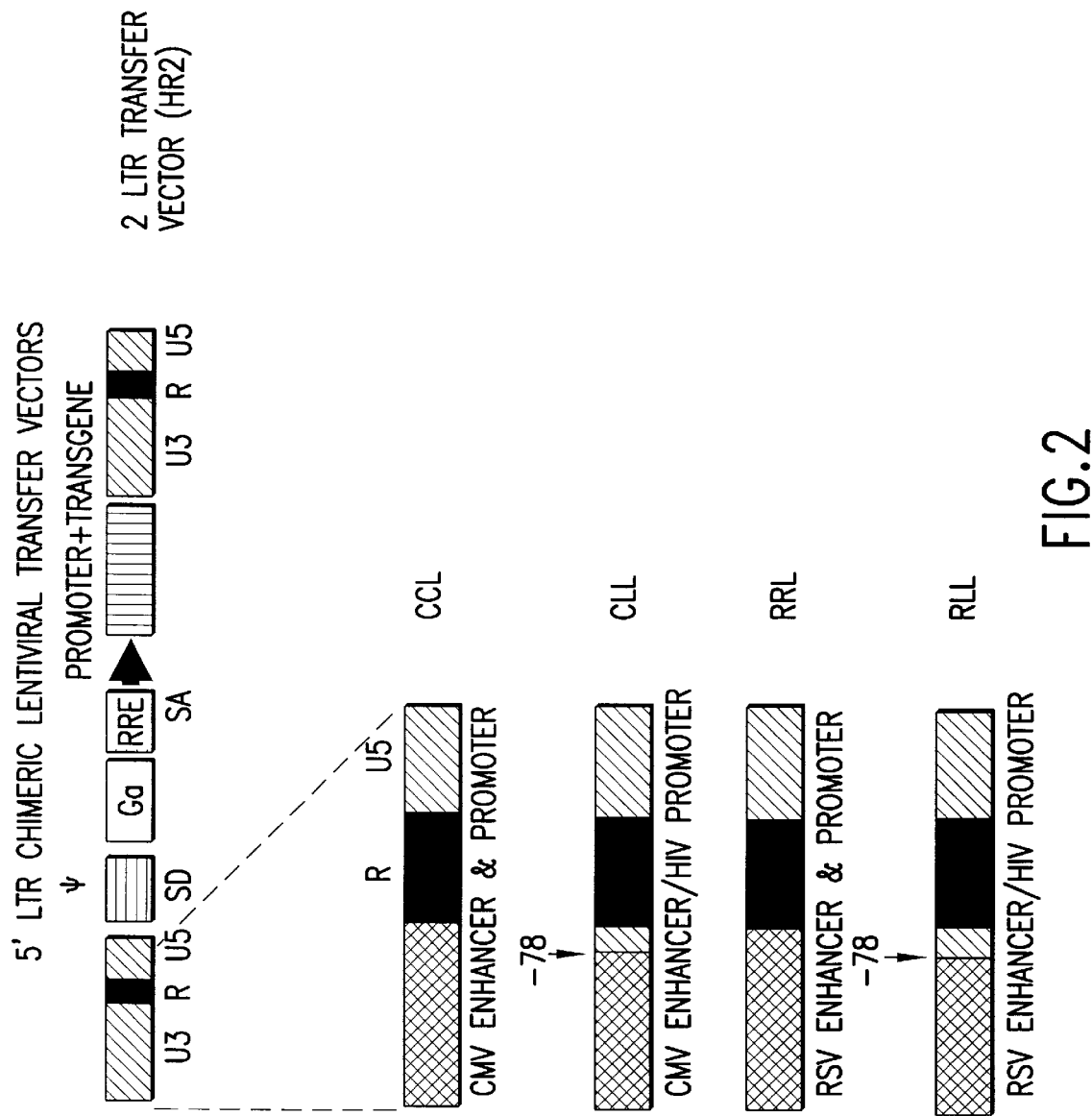
FIG. 2 depicts additional lentivirus vectors. CMV is cytomegalovirus. Otherwise, the symbols are as found in the legend to FIG. 1.

The enhancer or the enhancer and promoter regions of the 5' LTR were substituted with the enhancer or the enhancer and promoter of the human cytomegalovirus (CMV) or murine Rous sarcoma virus (RSV), respectively, see FIG. 2 for a schematic of the constructs and the code names of the hybrid vectors. The CCL and RRL vectors have complete substitution of the 5' U3 region.

The control lentivector HR2 and the panel of 5' hybrids were compared in producer cells transfected with the transfer vector, and with or without packaging constructs, which provide the tat transactivator. The transcriptional level of the four chimeric vectors is higher than that of a control lentivector both in the presence and in the absence of the packaging construct. All chimeric vectors efficiently transfer the transgene into target cells and the RRL vector performs as well as the control HR2 vector. Finally, integration of the vector in target cells was confirmed by examining transduced cells at an early and a later passage after transduction. No decrease was observed in the percentage of transgene-positive cells indicating that the vector had been integrated.

The high level of expression of the 5' LTR modified transfer vector RNA obtained in producer cells in the absence of a packaging construct indicates the producing vector is functional in the absence of a functional tat gene. Functional deletion of the tat gene as indicated for the packaging plasmid disclosed hereinabove would confer a higher level of biosafety to the lentiviral vector system given the number of pathogenetic activities associated with the tat protein. Thus, a lentiviral vector of significantly improved biosafety is a SIN transfer vector that has no wild-type copy of the HIV LTR either at the 5' or at the 3' end, which is used in conjunction with tat-less packaging vectors as described herein.

Viral supernatants are harvested using standard techniques such as filtration of supernatants 48 hours post transfection. The viral titer is determined by infection of, for example, $10^6$ NIH 3T3 cells or $10^5$ HeLa cells with an appropriate amount of viral supernatant, in the presence of 8 µg/ml polybrene (Sigma Chemical Co., St. Louis, Mo.). Forty-eight hours later, the transduction efficiency is assayed.

Thus, the instant invention provides methods and means for producing high titer recombinant virus. Those virus particle preparations can be used to infect target cells using techniques known in the art. Thus the instant invention will find use in ex vivo gene therapy applications wherein target cells are removed from a host, transformed in culture practicing known techniques and then returned to the host.

The invention now having been described in detail, provided hereinbelow are non-limiting examples demonstrating various embodiments of the instant invention.

EXAMPLE 1

Construction of Lentiviral Packaging Plasmids

The lentiviral packaging plasmids were derived from the plasmid pCMVΔR8.9 (ΔVprΔVifΔVpuΔNef) described previously in Zufferey et al., supra. All the remaining sequences of the nef gene in pCMVΔR8.9 were removed by digesting with XhoI and BstEII, filing in with Klenow and religating. The construction deleted 100 basepairs, joining the truncated env reading frame of HIV-1 to the genomic insulin polyadenylation site and yielding the plasmid pCMVΔR8.73.

In another embodiment of the invention, 133 basepairs of CMV-derived sequences downstream of the CMV promoter were deleted in the plasmid pCMVΔR8.73. That sequence contains a splice donor site and it was removed by digestion of the plasmid pCMVΔR8.73 with SacII and religation of the larger fragment, obtaining the plasmid pCMVΔR8.74.

In another embodiment of the invention, all the HIV-derived sequences remaining in the plasmid pCMVΔR8.74 upstream of the initiating codon of the gag gene were removed, except for the consensus 5' splice donor site. At the same time, the sequence upstream of the gag gene was changed for optimal translation efficiency obtaining the plasmid pCMVΔR8.75. pCMVΔR8.75 was derived from pCMVΔR8.74 by replacing the 94 bp SstII-ClaI fragment with an SstII-ClaI oligonucleotide linker consisting of, 5'-GGGACTGGTGAGTGAATTCGAGATCTGCCGCCG CCATGGGTGCGAGAGCGTCAGTA TTAAGCGGGGGAGAATTAGAT-3' (SEQ ID NO: 1) and 5'-CGATCTAATTCTCCCCCGCTTAATACTGACGCT CTCGCACCCATGGCGGCGGCAGA TCTCGAATTCACTCACCAGTCCCGC-3' (SEQ ID NO: 2).

In another embodiment of the invention, an inducible packaging construct was obtained by replacing the PstI-SacII fragment of pCMVΔR8.74 containing the CMV promoter with seven tandem copies of the tetracycline operator sequences linked to a minimal CMV promoter. The tet-regulated packaging plasmid pTet ΔR8.74 was obtained.

EXAMPLE 2

Construction of Lentiviral Transfer Vectors

The lentiviral transfer vector plasmids were derived from the plasmid pHR'-CMV-LacZ described previously in Naldini et al. (Sci. (1996) 272:263–267). pHR2 is a lentiviral transfer vector in which 124 bp of nef sequences upstream of the 3' LTR in pHR' were replaced with a polylinker both to reduce HIV1 sequences and to facilitate transgene cloning. pHR2 was derived from pHR'-CMV-LacZ by replacing the 4.6 kb ClaI-StuI fragment with the 828 bp ClaI-StuI fragment generated by PCR using pHR'-CMV-LacZ as the template and the oligonucleotide, 5'-CCATCGATC ACGAGACTAGTCCTACGTATCCCCGGGGAC GGGATCCGCGGAATTCC GTTTAAGAC-3' (SEQ ID NO: 3) and 5'-TTATAATGTCAAGGCCTCTC-3' (SEQ ID NO: 4) in a three part ligation with a 4.4 kb StuI-NcoI fragment and a 4.5 kb NcoI-ClaI fragment from pHR'-CMV-LacZ.

In another embodiment of the invention, pHR3 is a lentiviral transfer vector in which 148 bp of env coding sequences (including an ATG) upstream of the Rev Response Element (RRE) in pHR2 were deleted. pHR3 was derived from pHR2 by replacing the 893 bp NotI-SpeI fragment of pHR2 with a 747 bp NotI-SpeI fragment generated by PCR using pHR2 as the template with oligonucleotide primers 5'-GCGGCCGCAGGAGCTTTGTTCCTTGG-3' (SEQ ID NO: 5) and 5'-TACGTAGGACTAGTCTCG-3' (SEQ ID NO: 6).

In another embodiment of the invention, pHR5 is a lentiviral transfer vector in which 310 bp gag coding sequences (all gag coding sequences downstream from amino acid 15 of the Gag protein) were deleted from pHR2.

pHR5 was derived by digestion of pHR2 with NruI, addition of a NotI linker (synthetic oligonucleotide 5'-TTGCGGCCGCAA-3', SEQ ID NO: 7), digestion with NotI to excise the 310 bp fragment, followed by religation.

In another embodiment of the invention, pHR6 is a lentiviral vector in which the 5' splice donor signal was mutated (TGGT to TGAT) to enhance production of full-length transcripts capable of being packaged. pHR6 was derived from pHR5 by replacing the 239 bp AflII-ApoI fragment with a 239 bp AflII-ApoI fragment generated by PCR using a pHR2 as the template with oligonucleotide primers 5'-CCACTGCTTAAGCCT-3' (SEQ ID NO: 8) and 5'-CAAAATTTTTGGCGTACTCATCAGTCGCCGCCC CTCG-3' (SEQ ID NO: 9).

All PCR fragments were generated by first cloning the PCR reaction product directly into the TA cloning vector pCR2.1 (Invitrogen) followed by sequence verification and excision with the appropriate enzymes.

EXAMPLE 3

Construction of 5' LTR Chimeric Lentiviral Transfer Vectors

In another embodiment of the invention, the 5' LTR of the lentiviral vector contains the enhancer and promoter from the U3 region of the Rous Sarcoma Virus (RSV) joined to the R region of HIV-1 (plasmid pRRL).

pRRL is a lentiviral transfer vector in which the enhancer and promoter (nucleotides −233 to −1 relative to the transcriptional start site) of RSV is precisely fused to the R region of HIV-1 using an oligonucleotide linker. pRRL was derived from plasmids pRT43.RSV.F3, see WO97/07225, and pHR2 by replacing the 3.4 kb EcoRI-HpaI fragment of pRT43.RSV.F3 with the 0.67 kb BglII-NotI fragment from pHR2 and the 1.7 kb NotI-StuI fragment from pHR2 along with a synthetic EcoRI-BglII oligonucleotide linker consisting of oligonucleotides 5'-AATTGCCGCATTGCA GAGATATTGTATTTAAGTGCCTAGCTCGATACA ATAAACGGGTCTCTCTGGTTAGACCA-3' (SEQ ID NO: 10) and 5'-GATCTGGTCTAACCAGAGAGA CCCGTTTATTGTATCGAGCTAGGCACTTAAATACA ATATCTCTGCAATGCGGC-3' (SEQ ID NO: 11).

In another embodiment of the invention, the 5' LTR of the lentiviral vector contains the enhancer (nucleotides −233 −− 50 relative to the transcriptional start site) of the Rous Sarcoma Virus (RSV) joined to the promoter region (from the position −78 bp relative to the transcriptional start site) of HIV-1 (plasmid PRLL).

pRLL is a lentiviral transfer vector in which the enhancer of RSV is fused to the promoter region of HIV-1 using an oligonucleotide linker. pRLL was derived from plasmids pRT43.RSV.F3 and pHR2 by replacing the 3.4 kb EcoRI-HpaI fragment of pRT43.RSV.F3 with the 0.724 kb AlwNI-NotI fragment from pHR2 and the 1.7 kb NotI-StuI fragment from pHR2 along with a synthetic EcoRI-AlwNI oligonucleotide linker consisting of the oligo, 5'-AATTGGAGGCGTGGCCTGGGCGGGACTGGG GAGTGGCGAGCCCTCAGATC-3' (SEQ ID NO: 12) and the oligonucleotide, 5'-CTGAGGGCTCGCCACTCC CCAGTCCCGCCCAGGCCACGCCTCC-3' (SEQ ID NO: 13)

In another embodiment of the invention (plasmid pCCL), the 5' LTR of the lentiviral vector contains the immediate early enhancer and promoter (nucleotides −673 to −1, relative to the transcriptional start site according to Boshart et al. (Cell (1985) 41:521–530), of human Cytomegalovirus (CMV) joined to the R region of HIV-1. pCCL was derived from plasmids pRT43.2F3 (U.S. Pat. No. 5,686,279) and pHR2 by replacing the 3.8 kb SstI-HpaI fragment of pRT43.2F3 with the 1.7 kb BglII-NotI fragment from pHR2 and the 1.7 kb NotI-StuI fragment from pHR2 along with a synthetic SstI-BglII oligonucleotide linker consisting of the oligonucleotides, 5'-CGTTTAGTGAACCGGGGT CTCTCTGGTTAGACCA-3' (SEQ ID NO: 14) and 5'-GATCTGGTCTAACCAGAGAGACCCCGGTTCACT AAACGAGCT-3' (SEQ ID NO: 15).

In another embodiment of the invention, (plasmid pCLL), the 5'LTR of the lentiviral vector contains the enhancer nucleotides −220−−673 relative to the transcriptional start site of Cytomegalovirus (CMV) joined to the promoter region (from position −78 bp relative to the transcriptional start site) of HIV-1. pCLL was derived from plasmids pRT43.2F3 and pHR2 by replacing the 3.6 kb NcoI-HpaI fragment of pRT43.2F3 with the 0.724 kb AlwNI-NotI fragment from pHR2 and the 1.7 kb NotI-StuI fragment from pHR2 along with a synthetic NcoI-AlwNI oligonucleotide linker consisting of oligo, 5'-CATGGA GGCGTGGC-CTGGGCGGGACTGGGGAGTGGCGAGCCC TCAGATC-3' (SEQ ID NO: 16) and the oligonucleotide, 5'-CTGAGGGCTCGCCACTCCCCAGTCCCGCCCAGG CCACGCCTC-3' (SEQ ID NO: 17).

EXAMPLE 4

Construction of Self-Inactivating Lentiviral Vectors pRRL.SIN-18 was derived from pRRL by deleting the 400 bp EcoRV-PvuII fragment in the 3' LTR by digestion and religation.

pRRL.SIN-36 was derived from pRRL by replacing the 493 bp BbsI-AlwNI fragment in the 3' LTR with an oligonucleotide linker consisting of synthetic oligonucleotides, 5'-GATATGATCAGATC-3' (SEQ ID NO: 18) and 5'-CTGATCA-3' and a three part ligation along with a 0.54 kb AlwN-AvrII fragment and a 6.1 kb AvrII-BbsI fragment from PRRL.

pRRL.SIN-45 was derived from PRRL by replacing the 493 bp BbsI-AlwNI fragment in the 3' LTR with an oligonucleotide linker consisting of synthetic oligonucleotides, 5'-GATATGATCAGAGCCCTCAGATC-3' (SEQ ID NO: 19) and 5'-CTGAGGGCTCTGATCA-3' (SEQ ID NO: 20) in a three part ligation along with a 0.54 kb AlwNl-AvrII fragment and a 6.1 kb AvrII-BbsI fragment from pRRL.

pRRL.SIN-78 was derived from PRRL by replacing the 493 bp BbsI-AlwNI fragment in the 3'LTR with an oligonucleotide linker consisting of, 5'-GATATGATC AGGAG-GCGTGGCCTGGGCGGGACTGGGGAGTGG CGAGCCCTCAGATC-3' (SEQ ID NO: 21) and oligonucleotide 5'-CTGAGGGCTCGCCACTCCCCAGTCCCG CCCAGGCCACGCCTCCTGATCA-3' (SEQ ID NO: 22) in a three part ligation along with a 0.54 kb AlwNI-AvrII fragment and a 6.1 kb AvrII-BbsI fragment from pRRl.

EXAMPLE 5

Construction of Stable Lentiviral Packaging Cell 00-28 and of Stable Producers of Lentiviral Vector The 293G cell line was used to generate stable lentiviral packaging cells. 293G cells express the tet$^R$/VP16 transactivator from the MD cassette (CMV promoter and intervening sequences—exons 2 and 3, intron 2- and poly(A) site from the human β globin gene) and the VSV envelope from a minimal CMV promoter linked to a tandem repeat of seven tetracycline operator sites (tet$^0$). The expression of VSV G thus is regulated by the level of tetracycline in the culture medium, being suppressed in the presence of the antibiotic (Gossen & Bujard, Proc. Natl. Acad. Sci. USA (1992) 89:5547–5551); Ory et al., Proc. Natl. Acad. Sci. USA (1997) 93:11400–11406). The 293G cells were maintained routinely in DMEM/low glucose culture medium supplemented with 10% donor calf serum and containing 1 μg/ml tetracycline. A 15 cm plate of 293G cells were transfected using lipofectamine (GIBCO BRL) with 13.36 μg of the packaging plasmid pCMVΔR8.74 and 1.33 μg of the selection plasmid pZeoSV2. The medium was changed at 24 hr, and at 48 hr the cells were split into medium containing 250 μg/ml zeocin and 1 μg/ml tetracycline. After 3–4 weeks in selection, 250 clones were picked and transferred to 96 well plates and the medium screened for HIV-1 p24 Gag antigen by immunocapture using a commercially available kit. Fifty two p24 positive clones were grown up for further analysis. The best 5 clones were determined to have p24 values of 12–23 ng/ml. Of the 5 clones, 4 were positive for VSV.G expression after tetracycline withdrawal by Western blot analysis.

The four p24/VSV.G positive clones were analyzed further for the ability to package lentiviral transfer vectors. The clones were infected with transiently produced lentiviral vector (VSV.G pseudotype) containing an expression cassette for the Green Fluorescent Protein of A. victoria (GFP) driven by the CMV promoter, at a multiplicity of infection of 10 and in the presence of polybrene (8 μg/ml). The infected clones then were expanded and the tetracycline removed. After 72 hours of induction, a 24 hr medium collection was performed and the supernatants were filtered and flash frozen. The frozen supernatants were titered on naive HeLa cells for transduction of the GFP gene. By FACS analysis it was determined that the population of cells (designated 10-28) created from the infection of packaging clone 00-28 had the highest titer of 5×10$^4$ Transducing Units (T.U.)/ml.

Figure 3:
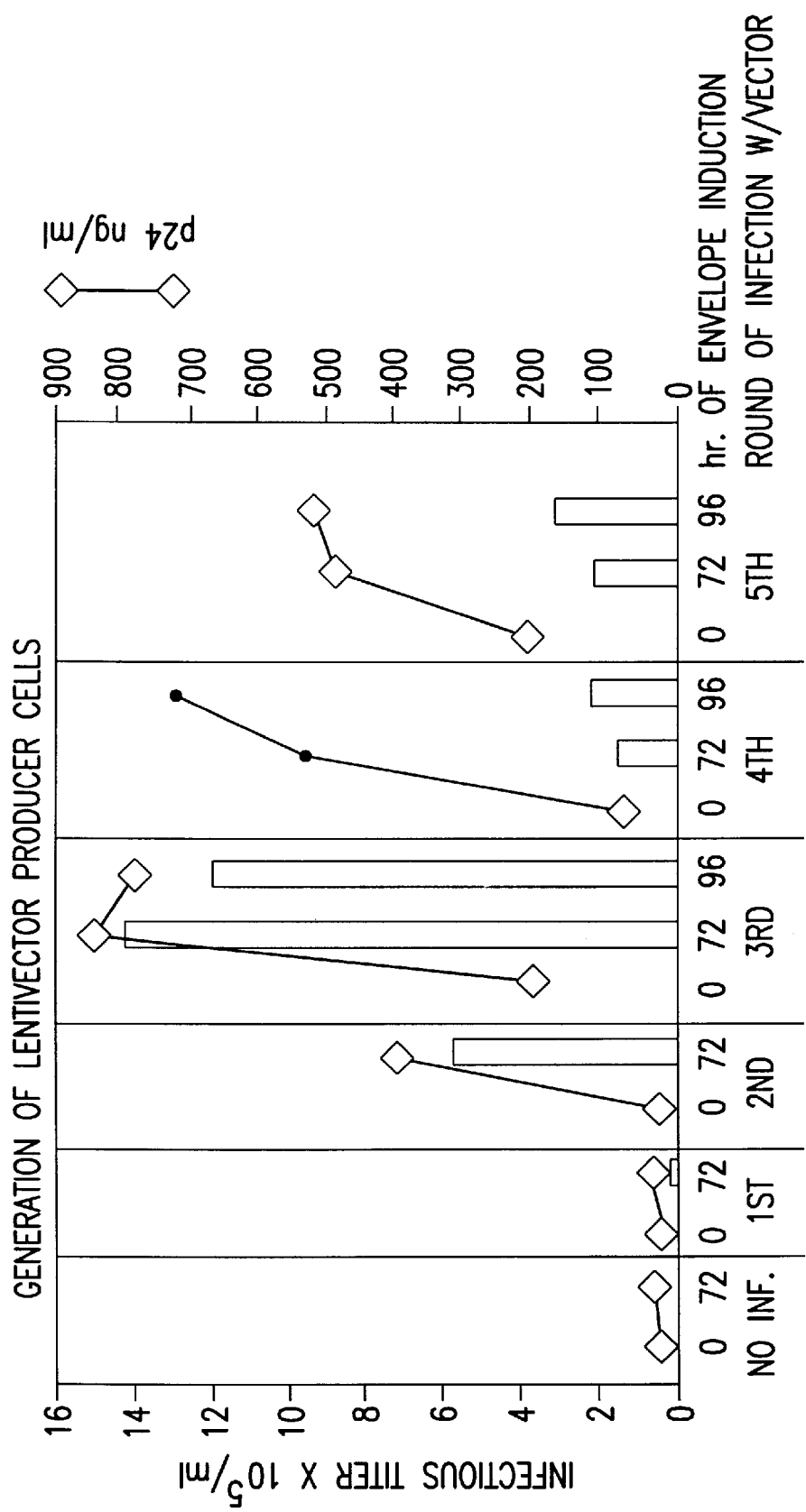
FIG. 3 is a graph depicting graded vector production with increasing amounts of transfer vector.

The infected packaging population, 10-28, was used for the creation of high titer producer clones of GFP lentiviral vector. 10-28 cells were sorted by FACS and the highest GFP expressing cells were retained and expanded. That population then was infected serially ("pinged") an additional 4 times with transiently produced GFP lentiviral (VSV.G pseudotype). After each infection the supernatants were collected after a 72–96 hr of VSV.G induction. Supernatants were titered on HeLa cells and analyzed for p24 content by immunocapture assay. Infectious titers peaked after the third ping reaching 1.5×10$^6$ T.U./ml (see FIG. 3). The population of cells from the third ping then were subcloned to isolate high titer vector producers.

All publications and patent applications cited in this specification are herein incorporated by reference in their entirety as if each individual publication or patent application were specifically and individually indicated to be incorporated by reference.

As will be apparent to those skilled in the art to which the invention pertains, the present invention may be embodied in forms other than those specifically disclosed above, for example to transfect and transduce other mammalian cell types, without departing from the spirit or essential characteristics of the invention. The particular embodiments of the invention described above, are, therefore, to be considered as illustrative and not restrictive. The scope of the present invention is as set forth in the appended claims rather than being limited to the examples contained in the foregoing description.

We claim:

1. A lentivirus transfer vector comprising a 5' LTR and a 3' LTR, each of which contains a U3 region, wherein a part or all of a regulatory element of the U3 region of the 5' LTR is replaced by another regulatory element, operable in a mammalian cell, which is not endogenous to said lentivirus.

2. The transfer transfer vector of claim 1, wherein one or more nucleotide bases of the U3 region of the 3' LTR are deleted.

3. The transfer vector of claim 1, wherein said regulatory element not endogenous to said lentivirus is a cytomegalovirus enhancer, promoter or enhancer/promoter.

4. The transfer vector of claim 1, wherein said regulatory element not endogenous to said lentivirus is a Rous sarcoma virus enhancer, promoter or enhancer/promoter.

5. The transfer vector of claim 1, wherein said transfer vector further comprises a heterologous gene.

6. The vector of claim 1, wherein said lentivirus is human immunodeficiency virus (HIV).

7. The transfer vector of claim 2, wherein said U3 region deleted is all of said U3 region except for a 5' terminal dinucleotide and an att sequence.

8. The transfer vector of claim 7, wherein said U3 region deleted includes a TATA box sequence.

9. The transfer vector of claim 6, wherein said HIV is HIV-1.

* * * * *

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
       (A) LENGTH: 77 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 1:

GGGACTGGTG AGTGAATTCG AGATCTGCCG CCGCCATGGG TGCGAGAGCG TCAGTATTAA    60

GCGGGGGAGA ATTAGAT                                                   77

(2) INFORMATION FOR SEQ ID NO: 2:

(i) SEQUENCE CHARACTERISTICS:
       (A) LENGTH: 81 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 2:

CGATCTAATT CTCCCCCGCT TAATACTGAC GCTCTCGCAC CCATGGCGGC GGCAGATCTC    60

GAATTCACTC ACCAGTCCCG C                                              81

(2) INFORMATION FOR SEQ ID NO: 3:

(i) SEQUENCE CHARACTERISTICS:
       (A) LENGTH: 65 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 3:

CCATCGATCA CGAGACTAGT CCTACGTATC CCCGGGGACG GGATCCGCGG AATTCCGTTT    60

AAGAC                                                                65

(2) INFORMATION FOR SEQ ID NO: 4:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 4:

TTATAATGTC AAGGCCTCTC                                                20

(2) INFORMATION FOR SEQ ID NO: 5:

(i) SEQUENCE CHARACTERISTICS:
       (A) LENGTH: 26 base pairs
       (B) TYPE: nucleic acid (C) STRANDEDNESS: single
            (D) TOPOLOGY: linear (ii) MOLECULE TYPE: DNA (xi) SEQUENCE DESCRIPTION: SEQ ID NO: 5:

GCGGCCGCAG GAGCTTTGTT CCTTGG                                             26

(2) INFORMATION FOR SEQ ID NO: 6:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 6:

TACGTAGGAC TAGTCTCG                                                      18

(2) INFORMATION FOR SEQ ID NO: 7:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 7:

TTGCGGCCGC AA                                                            12

(2) INFORMATION FOR SEQ ID NO: 8:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 8:

CCACTGCTTA AGCCT                                                         15

(2) INFORMATION FOR SEQ ID NO: 9:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 9:

CAAAATTTTT GGCGTACTCA TCAGTCGCCG CCCCTCG                                 37

(2) INFORMATION FOR SEQ ID NO: 10:

(i) SEQUENCE CHARACTERISTICS:
            (A) LENGTH: 74 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 10:

AATTGCCGCA TTGCAGAGAT ATTGTATTTA AGTGCCTAGC TCGATACAAT AAACGGGTCT    60

CTCTGGTTAG ACCA    74

(2) INFORMATION FOR SEQ ID NO: 11:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

GATCTGGTCT AACCAGAGAG ACCCGTTTAT TGTATCGAGC TAGGCACTTA AATACAATAT    60

CTCTGCAATG CGGC    74

(2) INFORMATION FOR SEQ ID NO: 12:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 12:

AATTGGAGGC GTGGCCTGGG CGGGACTGGG GAGTGGCGAG CCCTCAGATC    50

(2) INFORMATION FOR SEQ ID NO: 13:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 13:

CTGAGGGCTC GCCACTCCCC AGTCCCGCCC AGGCCACGCC TCC    43

(2) INFORMATION FOR SEQ ID NO: 14:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 14:

CGTTTAGTGA ACCGGGGTCT CTCTGGTTAG ACCA    34

(2) INFORMATION FOR SEQ ID NO: 15:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

GATCTGGTCT AACCAGAGAG ACCCCGGTTC ACTAAACGAG CT                42

(2) INFORMATION FOR SEQ ID NO: 16:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 16:

CATGGAGGCG TGGCCTGGGC GGGACTGGGG AGTGGCGAGC CCTCAGATC          49

(2) INFORMATION FOR SEQ ID NO: 17:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

CTGAGGGCTC GCCACTCCCC AGTCCCGCCC AGGCCACGCC TC                 42

(2) INFORMATION FOR SEQ ID NO: 18:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

GATATGATCA GATC                                                14

(2) INFORMATION FOR SEQ ID NO: 19:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 19:

GATATGATCA GAGCCCTCAG ATC                                      23

(2) INFORMATION FOR SEQ ID NO: 20:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 20:

CTGAGGGCTC TGATCA                                              16

(2) INFORMATION FOR SEQ ID NO: 21:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 21:

GATATGATCA GGAGGCGTGG CCTGGGCGGG ACTGGGGAGT GGCGAGCCCT CAGATC    56

(2) INFORMATION FOR SEQ ID NO: 22:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 22:

CTGAGGGCTC GCCACTCCCC AGTCCCGCCC AGGCCACGCC TCCTGATCA    49